United States Patent
Young et al.

(10) Patent No.: US 7,553,855 B2
(45) Date of Patent: Jun. 30, 2009

(54) COMPOSITIONS OF N-[2,4-BIS(1,1-DIMETHYLETHYL)-5-HYDROXYPHENYL]-1,4-DIHYDRO-4-OXOQUINOLINE-3-CARBOXAMIDE

(75) Inventors: Christopher R. Young, Waltham, MA (US); Charles William Rowe, Medford, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 88 days.

(21) Appl. No.: 11/748,073

(22) Filed: May 14, 2007

(65) Prior Publication Data

US 2008/0090864 A1 Apr. 17, 2008

Related U.S. Application Data

(60) Provisional application No. 60/799,795, filed on May 12, 2006.

(51) Int. Cl.
*A61K 31/47* (2006.01)

(52) U.S. Cl. .................................................. 514/312
(58) Field of Classification Search ................. 514/312
See application file for complete search history.

(56) References Cited

U.S. PATENT DOCUMENTS

| 7,001,770 B1 | 2/2006 | Atencio et al. |
| 2006/0074075 A1 * | 4/2006 | Hadida-Ruah et al. . 514/217.01 |
| 2008/0007109 A1 * | 1/2008 | Lawson et al. ........... 301/37.21 |
| 2008/0071095 A1 | 3/2008 | Hadida-Ruah et al. |
| 2008/0090864 A1 * | 4/2008 | Young et al. ................. 514/312 |

OTHER PUBLICATIONS

International Search Report for International Application No. PCT/US07/68857, (2008).

* cited by examiner

*Primary Examiner*—Raymond J Henley, III
(74) *Attorney, Agent, or Firm*—Honigman Miller LLP; Jonathan P. O'Brien

(57) ABSTRACT

Pharmaceutical compositions including N-[2,4-bis(1,1-dimethylethyl)-5-hydroxyphenyl]-1,4-dihydro-4-oxoquinoline-3-carboxamide (Compound 1) and methods of using such compositions are described herein.

24 Claims, 3 Drawing Sheets

COMPOSITIONS OF N-[2,4-BIS(1,1-DIMETHYLETHYL)-5-HYDROXYPHENYL]-1,4-DIHYDRO-4-OXOQUINOLINE-3-CARBOXAMIDE

CLAIM OF PRIORITY

This application claims priority under 35 USC §119(e) to U.S. Patent Application Ser. No. 60/799,795, filed on May 12, 2006, the entire contents of which are hereby incorporated by reference.

TECHNICAL FIELD OF THE INVENTION

The present invention relates to pharmaceutical compositions of N-[2,4-bis(1,1-dimethylethyl)-5-hydroxyphenyl]-1,4-dihydro-4-oxoquinoline-3-carboxamide and methods therewith.

BACKGROUND OF THE INVENTION

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/ctfr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl-channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. Infact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to a1-antitrypsin; non Piz variants), hereditary hemochromatosis, hoagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, Mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are Glycanosis CDG type 1, hereditary emphysema (due to α1-Antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to vasopvessin hormone/V2-receptor), nephrogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E. coli* (ETEC) having the K99 pilus antigen. Common viral causes of diarrhea include rotavirus and coronavirus. Other infectious agents include cryptosporidium, *giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for pharmaceutical compositions of modulators of CFTR activity that can be used to modulate the activity of CFTR in the cell membrane of a mammal.

There is a need for methods of treating CFTR-mediated diseases using such pharmaceutical compositions.

SUMMARY OF THE INVENTION

The present invention relates to pharmaceutical compositions of N-[2,4-bis(1,1-dimethylethyl)-5-hydroxyphenyl]-1, 4-dihydro-4-oxoquinoline-3-carboxamide (hereinafter "Compound 1") which has the structure below:

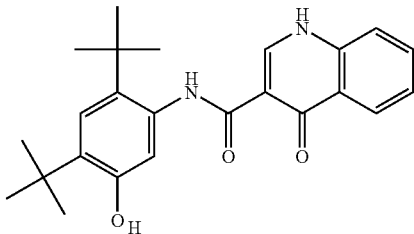

The pharmaceutical compositions of Compound 1 are useful for treating or lessening the severity of a variety of CFTR-mediated diseases.

DETAILED DESCRIPTION OF THE INVENTION

Figure 1:
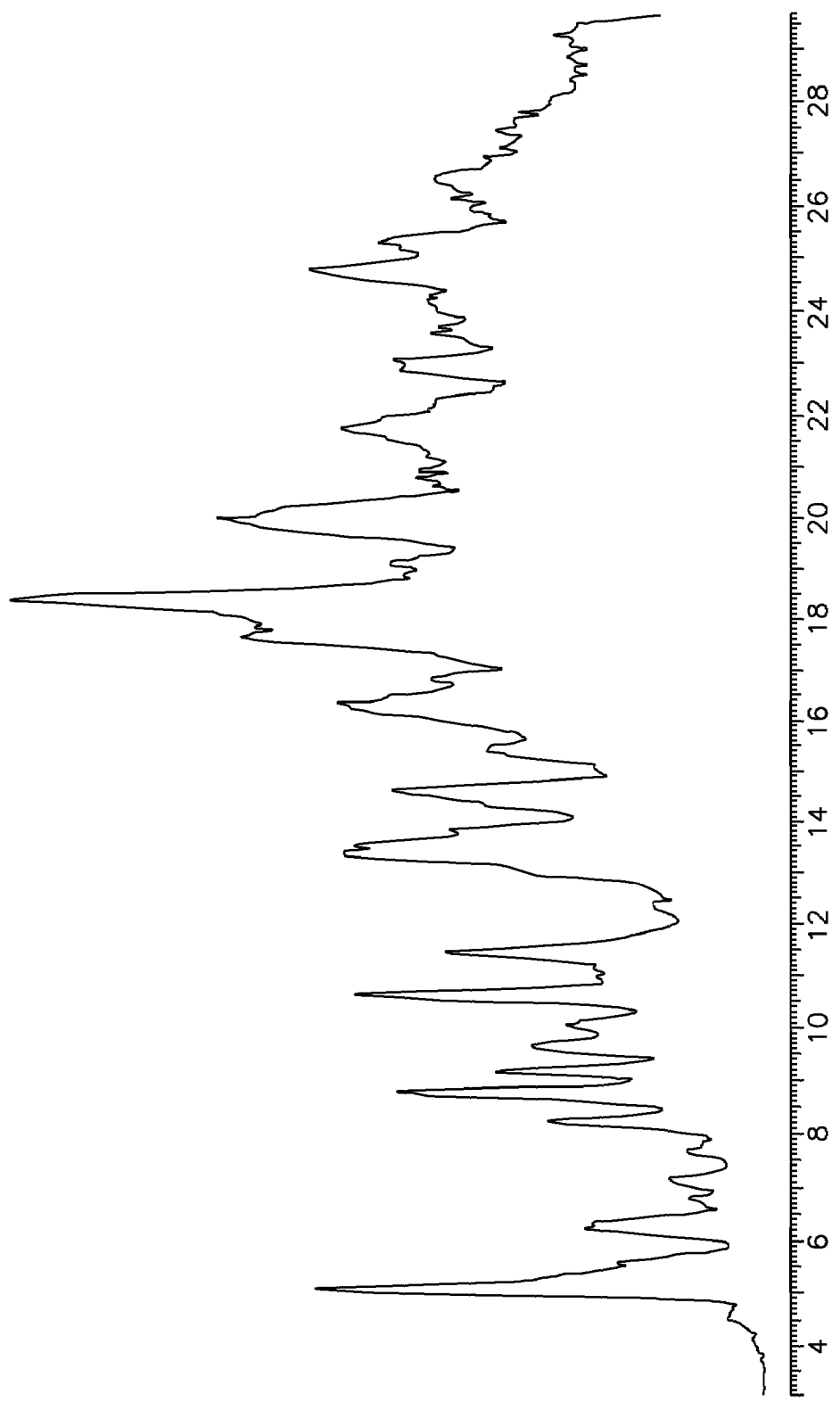
FIG. 1 is an X-Ray powder diffraction pattern of Compound 1.

According to one embodiment, the present invention provides a pharmaceutical composition comprising:
(i) N-[2,4-bis(1,1-dimethylethyl)-5-hydroxyphenyl]-1,4-dihydro-4-oxoquinoline-3-carboxamide (Compound 1) or a pharmaceutically acceptable salt thereof;
(ii) a suitable liquid PEG; and
(iii) optionally, a suitable viscosity enhancing agent.

As used herein, the phrase "suitable liquid PEG" means a polyethylene glycol polymer that is in liquid form at ambient temperature and is amenable for use in a pharmaceutical composition. Such suitable polyethylene glycols are well known in the art; see, e.g., http://www.medicinescomplete-.com/mc/excipients/current, which is incorporated herein by reference. Exemplary PEGs include low molecular weight PEGs such as PEG 200, PEG 300, PEG 400, etc. The number that follows the term "PEG" indicates the average molecular weight of that particular polymer. E.g., PEG 400 is a polyethylene glycol polymer wherein the average molecular weight of the polymer therein is about 400.

In one embodiment, said suitable liquid PEG has an average molecular weight of from about 200 to about 600. In another embodiment, said suitable liquid PEG is PEG 400 (for example a PEG having a molecular weight of form about 380 to about 420 g/mol).

In another embodiment, the present invention provides a pharmaceutical composition comprising Compound 1 or a pharmaceutically acceptable salt thereof, propylene glycol; and, optionally, a suitable viscosity enhancing agent.

In another embodiment, the pharmaceutical compositions of the present invention comprise a suitable viscosity enhancing agent agent. In one embodiment, the suitable viscosity enhancing agent is a polymer soluble in PEG. Such suitable viscosity enhancing agents are well known in the art, e.g., polyvinyl pyrrolidine (hereinafter "PVP"). PVP is characterized by its viscosity in aqueous solution, relative to that of water, expressed as a K-value (denoted as a suffix, e.g., PVP K20), in the range of from about 10 to about 120. See, e.g., http://www.medicinescomplete.com/mc/excipients/current.

Embodiments of PVP useful in the present invention have a K-value of about 90 or less. An exemplary such embodiment is PVP K30.

In one embodiment, the present invention provides a pharmaceutical composition comprising:
(i) N-(5-hydroxy-2,4-ditert-butyl-phenyl)-4-oxo-1H-quinoline-3-carboxamide (Compound 1) or a pharmaceutically acceptable salt thereof;
(ii) PEG 400; and
(iii) PVP K30.

In another embodiment, the present invention provides a pharmaceutical composition, wherein said N-(5-hydroxy-2,4-ditert-butyl-phenyl)-4-oxo-1H-quinoline-3-carboxamide is present in an amount from about 0.01% w/w to about 6.5% w/w.

In another embodiment, the present invention provides a pharmaceutical composition, wherein said PEG is present in an amount from about 87.5% w/w to about 99.99% w/w.

In another embodiment, the present invention provides a pharmaceutical composition, wherein said PVP K30 is present in an amount between 0% w/w to about 6% w/w.

In another embodiment, the present invention provides a pharmaceutical composition, wherein said composition comprises PEG 400 (e.g., from about 97.8 to about 98.0% w/w, for example, about 97.88% w/w), PVP K30 (e.g., from about 1.9 to about 2.1% w/w, for example, about 2.0% w/w), and Compound 1 (e.g., from about 0.10 to about 0.15% w/w, for example, about 0.13% w/w).

In another embodiment, the present invention provides a pharmaceutical composition, wherein said composition comprises PEG 400 (e.g., from about 97.5 to about 98.0% w/w, for example, about 97.75% w/w), PVP K30 (e.g., from about 1.8 to about 2.2% w/w, for example, about 2.0% w/w), and Compound 1 (e.g., from about 0.2 to about 0.3% w/w, for example, about 0.25% w/w).

In another embodiment, the present invention provides a pharmaceutical composition, wherein said composition comprises PEG 400 (e.g., from about 97.2 to about 97.8, for example, about 97.50% w/w), PVP K30 (e.g., from about 1.8 to about 2.2% w/w, for example, about 2.0% w/w), and Compound 1 (e.g., from about 0.4 to about 0.6% w/w, for example, about 0.50% w/w).

In another embodiment, the present invention provides a pharmaceutical composition, wherein said composition comprises PEG 400 (e.g., from about 96.5 to about 97.5% w/w, for example, about 97.0% w/w), PVP K30 (e.g., from about 1.8 to about 2.2% w/w, for example, about 2.0% w/w), and Compound 1 (e.g., from about 0.9 to about 1.1% w/w, for example, about 1.0% w/w).

In another embodiment, the present invention provides a pharmaceutical composition, wherein said composition comprises PEG 400 (e.g., from about 96.60 to about 96.65% w/w, for example, about 96.63% w/w), PVP K30 (e.g., from about 1.8 to about 2.2% w/w, for example, about 2.0% w/w), and Compound 1 (e.g., from about 1.30 to about 1.45% w/w, for example, about 1.38% w/w).

In another embodiment, the present invention provides a pharmaceutical composition, wherein said composition comprises PEG 400 (e.g., from about 96.0 to about 96.3% w/w, for example, about 96.12% w/w), PVP K30 (e.g., from about 1.8 to about 2.0% w/w, for example, about 2.0% w/w), and Compound 1 (e.g., from about 1.8 to about 2.2% w/w, for example, about 1.88% w/w).

In another embodiment, the present invention provides a pharmaceutical composition, wherein said composition comprises PEG 400 (e.g., from about 95.5 to about 96.0% w/w, for example, about 95.75% w/w), PVP K30 (e.g., from about 1.8 to about 2.2% w/w, for example, about 2.0% w/w), and Compound 1 (e.g., from about 2.0 to about 2.5% w/w, for example, about 2.25% w/w).

In another embodiment, the present invention provides a pharmaceutical composition, wherein said composition comprises PEG 400 (e.g., from about 95 to about 96% w/w, for example, about 95.5% w/w), PVP K30 (e.g., from about 1.8 to about 2.2% w/w, for example, about 2.0% w/w), and Compound 1 (e.g., from about 2.3 to about 2.7% w/w, for example, about 2.50% w/w)

In another embodiment, the present invention provides a pharmaceutical composition, wherein said composition comprises PEG 400 (e.g., from about 94.5 to about 94.8, for example, about 94.63% w/w), PVP K30 (e.g., from about 1.8 to about 2.2% w/w, for example, about 2.0% w/w), and Compound 1 (e.g., from about 3.5 to about 4.0% w/w, for example, about 3.38% w/w).

In another embodiment, the present invention provides a pharmaceutical composition, wherein said composition comprises PEG 400 (e.g., from about 93.5 to about 94.5% w/w, for example, about 94.0% w/w), PVP K30 (e.g., from about 1.8 to about 2.2% w/w, for example, about 2.0% w/w), and Compound 1 (e.g., from about 3.7 to about 4.3% w/w, for example, about 4.0% w/w).

In one embodiment, the present invention provides a pharmaceutical composition comprising:
(i) N-(5-hydroxy-2,4-ditert-butyl-phenyl)-4-oxo-1H-quinoline-3-carboxamide (Compound 1) or a pharmaceutically acceptable salt thereof;
(ii) a suitable PEG lipid; and
(iii) PVP.

In some embodiments, the PEG lipid has an average molecular weight of from about 400 to about 600, for example, PEG 400. In some embodiments, the PVP is PVP K30.

According to another embodiment, the pharmaceutical compositions of the present invention comprise a therapeutically effective amount of Compound 1. The phrase "therapeutically effective amount" is that amount effective for treating or lessening the severity of any of the diseases, conditions, or disorders recited below.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. E.g., Compound 1 may exist as tautomers:

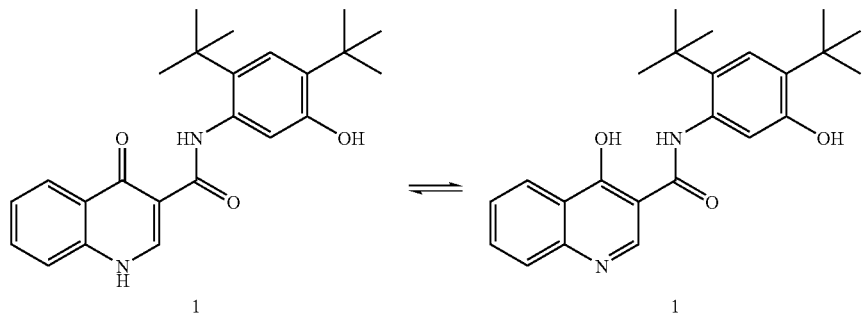

Unless otherwise stated, structures depicted herein are also meant to include compounds that differ only in the presence of one or more isotopically enriched atoms. For example, compounds of formula (I), wherein one or more hydrogen atoms are replaced deuterium or tritium, or one or more carbon atoms are replaced by a 13C- or 14C-enriched carbon are within the scope of this invention. Such compounds are useful, for example, as analytical tools, probes in biological assays, or compounds with improved therapeutic profile.

Uses, Formulation and Administration

Pharmaceutically Acceptable Compositions

In another aspect of the present invention, pharmaceutically acceptable compositions are provided, wherein these compositions comprise an additional pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In one embodiment, the present invention provides a method of treating a CFTR mediated disease, condition, or disorder in a patient comprising the step of administering to a patient a pharmaceutical composition according to the present invention.

A "CFTR-mediated disease" as used herein is a disease selected from cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

According to an alternative embodiment, the present invention provides a method of treating cystic fibrosis comprising the step of administering to said mammal a pharmaceutical composition according to the present invention.

In certain embodiments, the pharmaceutically compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In one embodiment, the pharmaceutically acceptable compositions of the present invention are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, the pharmaceutically acceptable composition of the present invention are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic sufficiency or patients diagnosed with idiopathic pancreatitis and congenital bilateral absence of the vas deferens, or mild lung disease.

The exact amount of Compound 1 required in the pharmaceutical compositions of the present invention will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered orally at dosage levels of about 0.01 mg/kg to about 50 mg/kg and preferably from about 1 mg/kg to about 25 mg/kg, of subject body weight per day, one or more times a day, to obtain the desired therapeutic effect.

The pharmaceutical compositions of the present invention may additionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

It will also be appreciated that the pharmaceutically compositions of the present invention can be employed in combination therapies, that is, they can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a pharmaceutical composition of the present invention may be administered concurrently with another agent used to treat the same disorder), or they may achieve different effects (e.g., control of any adverse effects). As used herein, additional therapeutic agents normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In order that the invention described herein may be more fully understood, the following examples are set forth. It should be understood that these examples are for illustrative purposes only and are not to be construed as limiting this invention in any manner.

EXAMPLES

Methods & Materials
Differential Scanning Calorimetry (DSC)

DSC data was collected on a TA instrument Q1000 equipped with a 50 position autosampler. The energy and temperature calibration standard was indium. Samples were heated at a rate of 10° C./min between 20 and 35° C. A nitrogen purge at 30 ml/min was maintained over the sample.

Between 0.5 and 4 mg of sample was used and all samples run in a pinhole aluminium pan.

NMR

All spectra were collected on a Bruker 400 MHz equipped with autosampler. Samples were prepared in $d_6$-DMSO, unless otherwise stated.

XRPD (X-ray Powder Diffraction)
Bruker AXS C2 GADDS Diffractometer

X-ray powder diffraction patterns for the samples were acquired on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

Beam divergence, i.e. the effective size of the X-ray beam on the sample, was approximately 4 mm. A θ-θ continuous scan mode was employed with a sample to detector distance of 20 cm which gives an effective 2θ range of 3.2-29.8°. A typical exposure time of a sample would be 120 s.

Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat conducting compound. The sample was then heated to the appropriate temperature at ca. 20° C./minute and subsequently held isothermally for ca 1 minute before data collection was initiated.

Synthesis of N-(5-hydroxy-2,4-ditert-butyl-phenyl)-4-oxo-1H-quinoline-3-carboxamide (Compound 1)

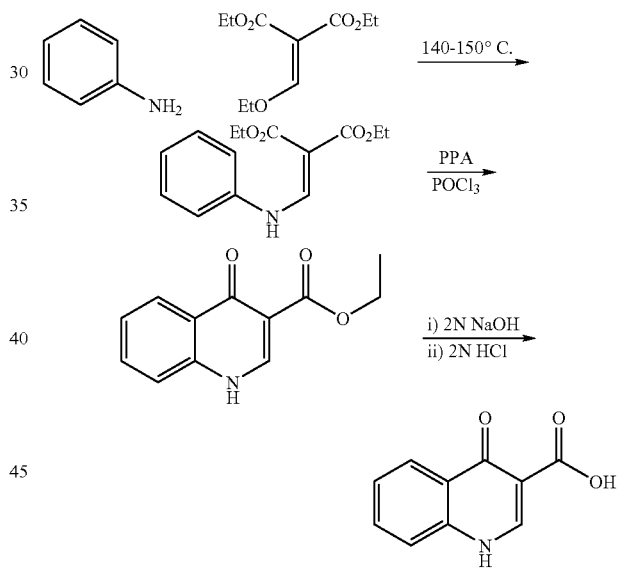

2-Phenylaminomethylene-malonic acid diethyl ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. $^1$H NMR (DMSO-$d_6$) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

4-Hydroxyquinoline-3-carboxylic acid ethyl ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous $Na_2CO_3$ solution, filtered, washed with water and dried. 4-Hydroxyquinoline-3-carboxylic acid ethyl ester was obtained as a pale brown solid (15.2 g, 70%). The crude product was used in next step without further purification.

4-Oxo-1,4-dihydroquinoline-3-carboxylic acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%). $^1$H NMR (DMSO-$d_6$) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

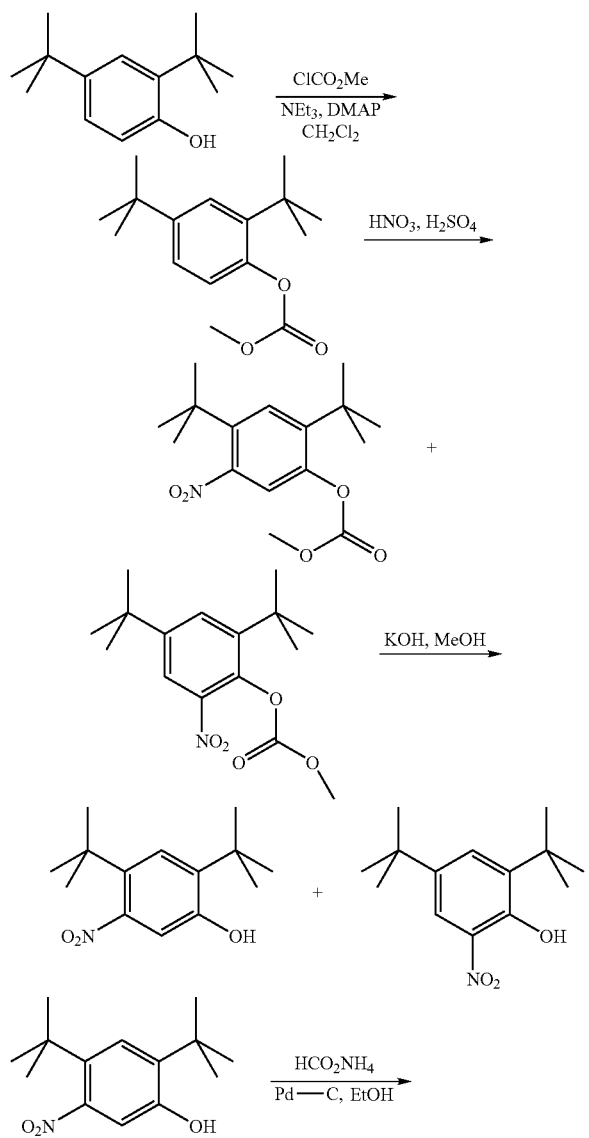

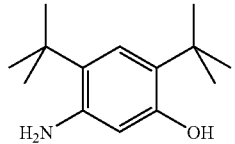

Carbonic acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), $Et_3N$ (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate-hexanes (~4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-$d_6$) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Carbonic acid 2,4-di-tert-butyl-5-nitro-phenyl ester methyl ester and Carbonic acid 2,4-di-tert-butyl-6-nitro-phenyl ester methyl ester To a stirring mixture of carbonic acid 2,4-di-tert-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried ($MgSO_4$), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

2,4-Di-tert-butyl-5-nitro-phenol and 2,4-Di-tert-butyl-6-nitro-phenol

The mixture of carbonic acid 2,4-di-tert-butyl-5-nitro-phenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried ($MgSO_4$), concentrated and purified by column chromatography (0-5% ethyl acetate-hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-$d_6$) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, $CDCl_3$) δ 11.48 (s, 1H), 7.98 (d, J=2.5 Hz, 1H), 7.66 (d, J=2.4 Hz, 1H), 1.47 (s, 9H), 1.34 (s, 9H).

5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-$d_6$) δ 8.64 (s, 1H, OH), 6.84 (s, 1H), 6.08 (s, 1H), 4.39 (s, 2H, $NH_2$), 1.27 (m, 18H); HPLC ret. time 2.72 min, 10-99% $CH_3CN$, 5 min run; ESI-MS 222.4 m/z $[M+H]^+$.

N-(5-hydroxy-2,4-ditert-butyl-phenyl)-4-oxo-1H-quinoline-3-carboxamide

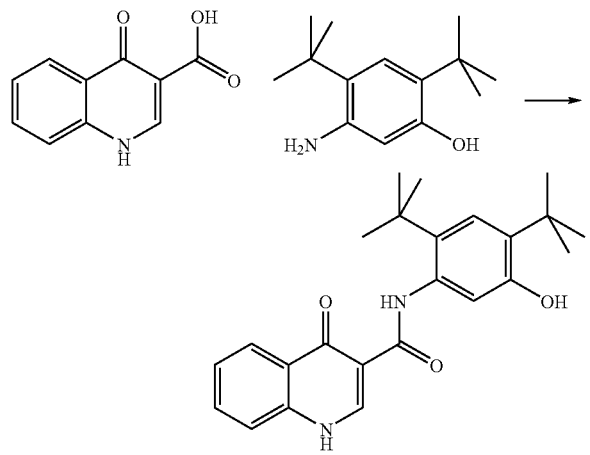

To a suspension of 4-oxo-1,4-dihydroquinolin-3-carboxylic acid (35.5 g, 188 mmol) and HBTU (85.7 g, 226 mmol) in DMF (280 mL) was added $Et_3N$ (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+ 190, 1.71 min), the solvent was removed in vacuo. EtOH was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystalate. $Et_2O$ was added to the material obtained above until a slurry was formed. The mixture was stirred on a rotovapor (bath temperature 25° C.) for 15 min without placing the system under vacuum. The mixture was filtered and the solid captured. This procedure was performed a total of five times. The solid obtained after the fifth precipitation was placed under vacuum overnight to provide 8 N-(5-hydroxy-2,4-ditert-butyl-phenyl)-4-oxo-1H-quinoline-3-carboxamide as a white powdery solid (38 g, 52%).

HPLC ret. time 3.45 min, 10-99% $CH_3CN$, 5 min run; $^1$H NMR (400 MHz, DMSO-$d_6$) δ 12.88 (s, 1H), 11.83 (s, 1H), 9.20 (s, 1H), 8.87 (s, 1H), 8.33 (dd, J=8.2, 1.0 Hz, 1H), 7.83-7.79 (m, 1H), 7.76 (d, J=7.7 Hz, 1H), 7.54-7.50 (m, 1H), 7.17 (s, 1H), 7.10 (s, 1H), 1.38 (s, 9H), 1.37 (s, 9H); ESI-MS 393.3 m/z $[M+H]^+$.

Set forth below is the characterizing data for Compound 1:

TABLE 2

| Cmd. No. | LC-MS M + 1 | LC-RT min |
|---|---|---|
| 1 | 393.2 | 3.71 |

Figure 2:
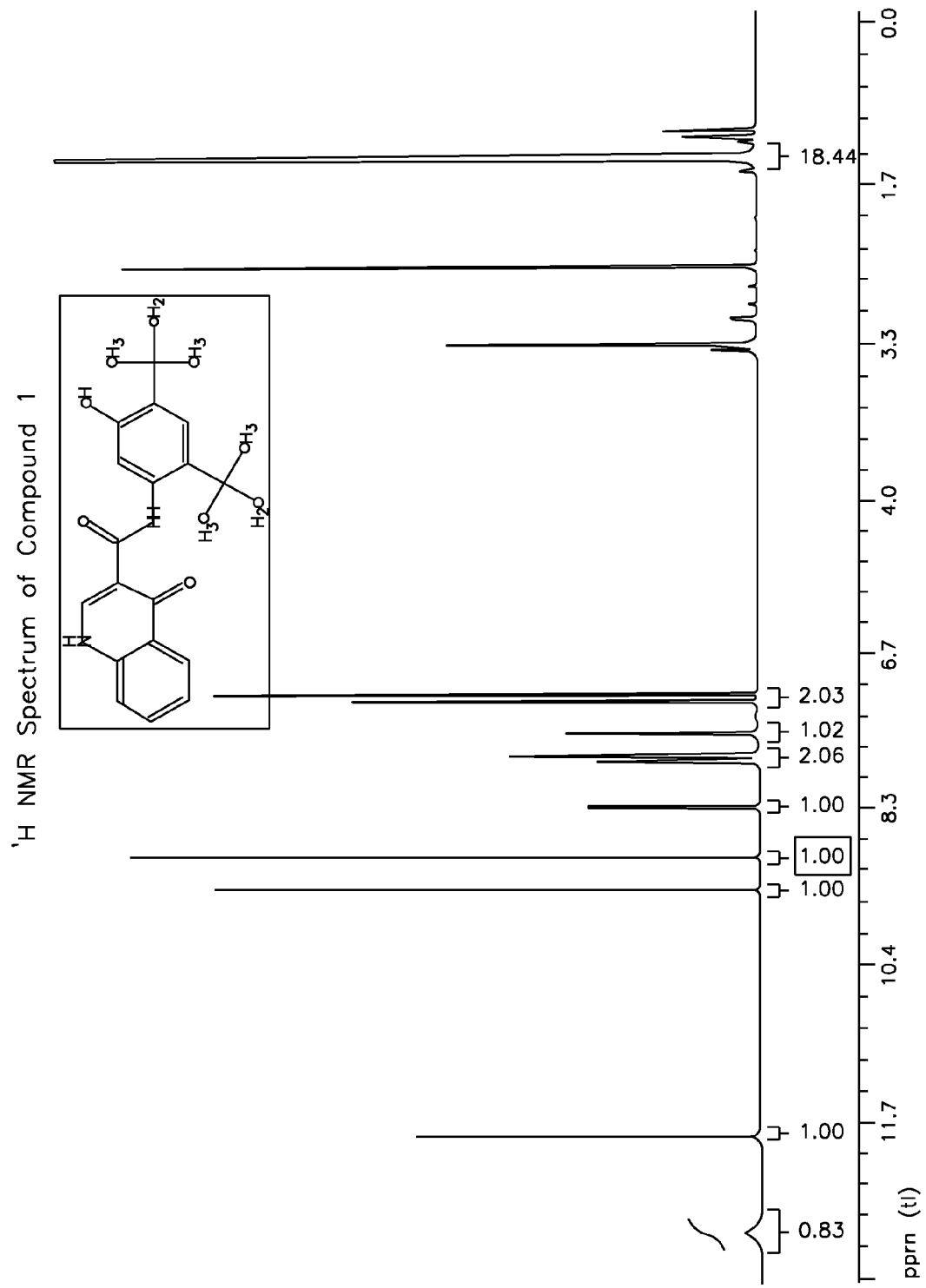
FIG. 2 is the $^1$H NMR spectrum of Compound 1.
Figure 3:
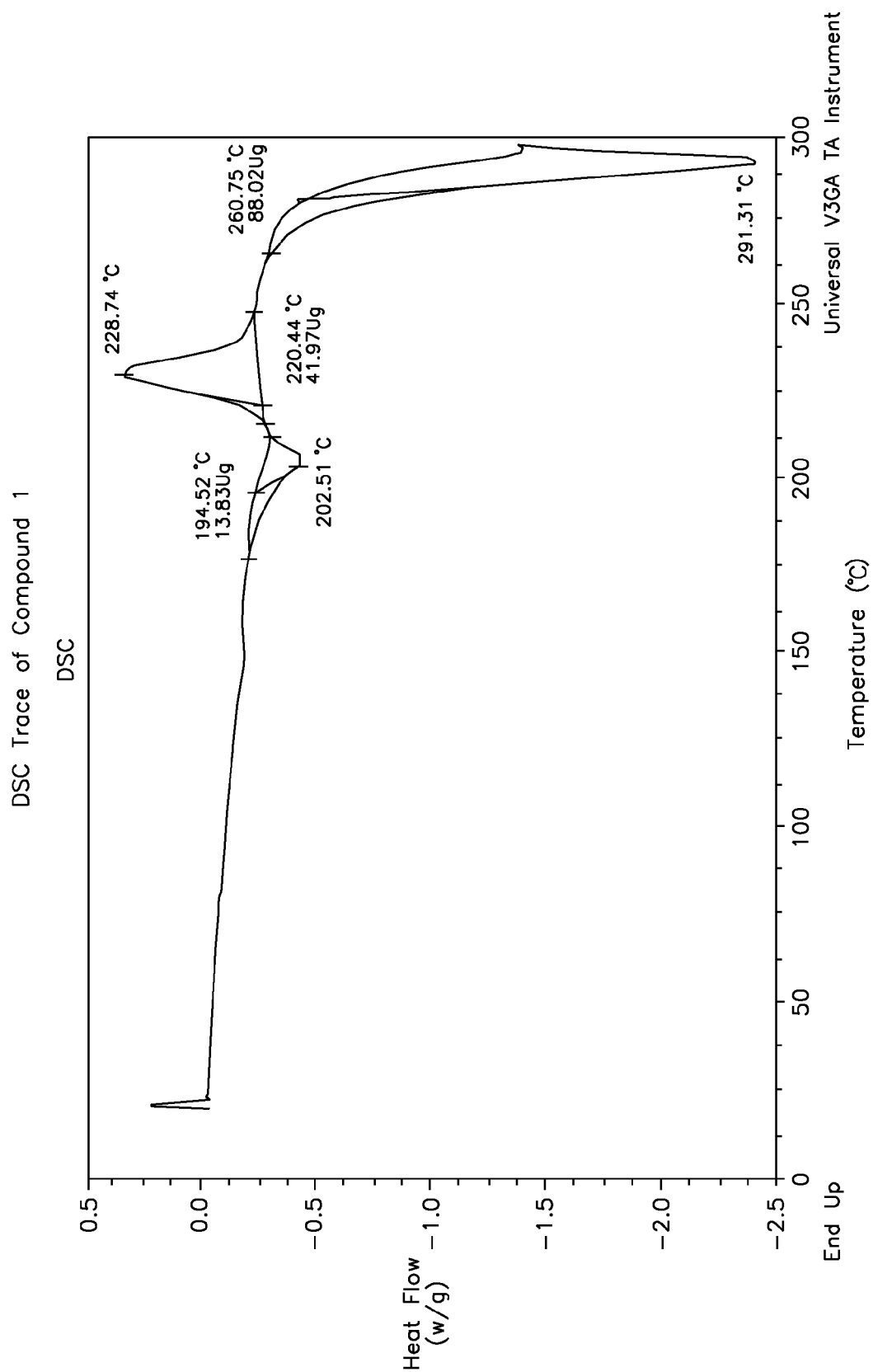
FIG. 3 is the DSC trace of Compound 1.

The XRPD spectrum of Compound 1 is shown in FIG. 1.
$^1$H NMR data for Compound 1 in shown in FIG. 2.
The DSC trace of Compound 1 is shown in FIG. 3.

Preparation of Pharmaceutical Compositions

Materials:
A Glass bottle for formulation preparation (250 cc amber glass with teflon lined lid)
Glass bottle for dose confirmation sample (30 cc amber glass with Teflon lined lid)
Stir Plate with temperature probe (ensure probe has been cleaned)
New magnetic stir bar
Spatulas for dispensing excipient and active.

Step 1: To a clean 250 cc amber glass bottle add the stir bar to the bottle and record the tare weight of the bottle, stir bar, label and cap. Tare the bottle with the label and stir bar.

Step 2: Dispense targeted amount of PEG400 into the bottle and accurately weigh. Place the bottle on stir plate and stir to form a small vortex at the surface of the liquid (~300-500 rpm or as necessary). Insert the cleaned temperature probe into the liquid to a depth of ~1 cm and raise the setpoint of the heater to 40° C. Cover the bottle opening with aluminum foil. Allow the PEG400 to stabilize at 40+/−5° C.

Step 3: Dispense the required amount of PVP K30 and add to the stirring PEG400. Add the PVP in a slow stream (over ~2-3 minutes) and allow the particles to disperse. If the particles clump, the dissolution will take longer. Cover the bottle opening with foil and continue stirring the mixture at 40+/−5° C. The mixture should be sampled at 10 minutes using a small transfer pipette to determine if the PVP has completely dissolved. The stirring solution should also be examined for large, undissolved clumps. If the solution is clear, proceed to the next step. If undissolved polymer remains, continue stirring. Check for dissolution every 10 minutes, with a maximum stirring time of 30 minutes total. When complete dissolution is observed, proceed to the next step. If complete dissolution is not observed within 30 minutes after PVP addition, terminate preparation, discard the material, and start the preparation from the beginning.

Step 4: Dispense the required amount of Compound 1 and add to the stirred PEP/PVP solution in a slow stream. Cover the bottle opening with foil and continue stirring the mixture at 40+/−5° C. The mixture should be sampled after 30 minutes using a small transfer pipette to determine if the Compound 1 has completely dissolved. If the solution is clear after 30 minutes, proceed to the next step. If undissolved Compound 1 remains, continue stirring. Check for dissolution every 30 minutes with a maximum stirring time of 300 minutes (5 hours) after addition of Compound 1. If complete dissolution is not observed within 300 minutes (5 hours) after addition of Compound 1, terminate preparation, discard the material, and start the preparation from the beginning.

Upon complete dissolution of the Compound 1, remove from the stir plate, and cap the bottle. The formulation should be maintained at room temperature until dosing, but must be dosed within 24 hours of preparation. If precipitation of VX-770 is observed, do not dose the solution.

Using the above method, the following ten pharmaceutical compositions in Table A were prepared:

TABLE A

| Composition # | % PEG 400 w/w | % PVP K30 w/w | % Cmpd 1 w/w | Amount of Cmpd 1 per 20 g dose (mg) |
|---|---|---|---|---|
| 1 | 97.875 | 2.0 | 0.125 | 25 |
| 2 | 97.750 | 2.0 | 0.250 | 50 |
| 3 | 97.500 | 2.0 | 0.500 | 100 |
| 4 | 97.000 | 2.0 | 1.000 | 200 |
| 5 | 96.625 | 2.0 | 1.375 | 275 |
| 6 | 96.125 | 2.0 | 1.875 | 375 |
| 7 | 95.750 | 2.0 | 2.25 | 450 |
| 8 | 95.500 | 2.0 | 2.500 | 500 |
| 9 | 94.625 | 2.0 | 3.375 | 675 |
| 10 | 94.000 | 2.0 | 4.000 | 800 |

What is claimed is:

1. A pharmaceutical composition comprising: N-(5-hydroxy-2,4-ditert-butyl-phenyl)-4-oxo-1H-quinoline-3-carboxamide; PEG 400; and PVP K30.

2. The pharmaceutical composition according to claim 1, wherein said N-(5-hydroxy-2,4-ditert-butyl-phenyl)-4-oxo-1H-quinoline-3-carboxamide is present in an amount between about 0.01% w/w to about 6.5% w/w.

3. The pharmaceutical composition according to claim 1, wherein said PEG is present in an amount between about 87.5% w/w to about 99.99% w/w.

4. The pharmaceutical composition according to claim 1, wherein said PVP K30 is present in an amount between 0% w/w to about 6% w/w.

5. The pharmaceutical composition according to claim 1, wherein said composition comprises PEG 400 (97.88% w/w), PVP K30 (2.0% w/w), and N-(5-hydroxy-2,4-ditert-butyl-phenyl)-4-oxo-1H-quinoline-3-carboxamide (0.13% w/w).

6. The pharmaceutical composition according to claim 1, wherein said composition comprises PEG 400 (97.75% w/w), PVP K30 (2.0% w/w), and N-(5-hydroxy-2,4-ditert-butyl-phenyl)-4-oxo-1H-quinoline-3-carboxamide (0.25% w/w).

7. The pharmaceutical composition according to claim 1, wherein said composition comprises PEG 400 (97.5% w/w), PVP K30 (2.0% w/w), and N-(5-hydroxy-2,4-ditert-butyl-phenyl)-4-oxo-1H-quinoline-3-carboxamide (0.5% w/w).

8. The pharmaceutical composition according to claim 1, wherein said composition comprises PEG 400 (97.0% w/w), PVP K30 (2.0% w/w), and N-(5-hydroxy-2,4-ditert-butyl-phenyl)-4-oxo-1H-quinoline-3-carboxamide (1.0% w/w).

9. The pharmaceutical composition according to claim 1, wherein said composition comprises PEG 400 (96.63% w/w), PVP K30 (2.0% w/w), and N-(5-hydroxy-2,4-ditert-butyl-phenyl)-4-oxo-1H-quinoline-3-carboxamide (1.38% w/w).

10. The pharmaceutical composition according to claim 1, wherein said composition comprises PEG 400 (96.13% w/w), PVP K30 (2.0% w/w), and N-(5-hydroxy-2,4-ditert-butyl-phenyl)-4-oxo-1H-quinoline-3-carboxamide (1.88% w/w).

11. The pharmaceutical composition according to claim 1, wherein said composition comprises PEG 400 (95.75% w/w), PVP K30 (2.0% w/w), and N-(5-hydroxy-2,4-ditert-butyl-phenyl)-4-oxo-1H-quinoline-3-carboxamide (2.25% w/w).

12. The pharmaceutical composition according to claim 1, wherein said composition comprises PEG 400 (95.5% w/w), PVP K30 (2.0% w/w), and N-(5-hydroxy-2,4-ditert-butyl-phenyl)-4-oxo-1H-quinoline-3-carboxamide (2.5% w/w).

13. The pharmaceutical composition according to claim 1, wherein said composition comprises PEG 400 (94.63% w/w), PVP K30 (2.0% w/w), and N-(5-hydroxy-2,4-ditert-butyl-phenyl)-4-oxo-1H-quinoline-3-carboxamide (3.38% w/w).

14. The pharmaceutical composition according to claim 1, wherein said composition comprises PEG 400 (94.0% w/w), PVP K30 (2.0% w/w), and N-(5-hydroxy-2,4-ditert-butyl-phenyl)-4-oxo-1H-quinoline-3-carboxamide (4.0% w/w).

15. A method of treating a CFTR mediated disease in a patient comprising the step of administering to said patient a pharmaceutical composition according to claim 1.

16. The method according to claim 15, wherein said disease is selected from cystic fibrosis, hereditary emphysema, hereditary hemochromatosis, a coagulation-fibrinolysis deficiency, Type 1 hereditary angioedema, a lipid processing deficiency, a lysosomal storage disease Crigler-Najjar type II, polyendocrinopathy/hyperinsulinemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, a neurodegenerative disease a polyglutamine neurological disorder, orders a spongiform encephalopathy, Fabry disease, Straussler-Scheinker syndrome, COPD, dry-eye disease and Sjogren's disease.

17. The method according to claim 16, wherein said disease is cystic fibrosis.

18. The method according to claim 15, wherein said pharmaceutical composition is administered to a patient in need thereof once a day.

19. The method according to claim 16 wherein the coagulation-fibrinolysis deficiency is protein C deficiency.

20. The method according to claim 16 wherein the lipid processing deficiency is familial hypercholesterolemia, Type 1 chylomicronemia or abetalipoproteinemia.

21. The method according to claim 16 wherein the lysosomal storage disease is I-cell disease, pseudo-Hurler, mucopolysaccharidoses, Sandhoff disease, or Tay-Sachs.

22. The method according to claim 16 wherein the neurodegenerative disease is Alzheimer's disease, Parkinson's disease, amyotrophic lateral sclerosis, progressive supranuclear palsy, or Pick's disease.

23. The method according to claim 16 wherein the polyglutamine neurological disorder is Huntington's disease, spinocerebullar ataxia type I, spinal muscular atrophy, bulbar muscular atrophy, dentatorubal pallidoluysian, or myotonic dystrophy.

24. The method according to claim 16 wherein the spongiform encephalopathy is hereditary Creutzfeldt-Jakob disease.

* * * * *